United States Patent [19]

Jackson

[11] 4,419,903

[45] Dec. 13, 1983

[54] METHOD AND APPARATUS FOR DETECTING INSUFFICIENT LIQUID LEVELS

[75] Inventor: Delbert D. Jackson, Yorba Linda, Calif.

[73] Assignee: Beckman Instruments, Inc., Fullerton, Calif.

[21] Appl. No.: 350,697

[22] Filed: Feb. 22, 1982

[51] Int. Cl.³ .............................................. G01N 35/08
[52] U.S. Cl. ................................. 73/864.01; 250/573; 250/574; 422/82
[58] Field of Search ........... 73/864.12, 864.21, 864.22, 73/864.23, 864.24, 864.25, 864.01; 422/81, 82; 250/273, 274, 276, 277

[56] References Cited

U.S. PATENT DOCUMENTS

| | | | |
|---|---|---|---|
| 3,422,667 | 1/1969 | Hrdina | 422/82 |
| 3,600,953 | 8/1971 | Isreeli et al. | 422/82 |
| 3,636,360 | 1/1972 | Oishi | 250/577 |
| 3,812,482 | 5/1974 | Clark | 250/573 |
| 3,908,129 | 9/1975 | Akers | 250/574 |
| 4,002,269 | 1/1977 | Negersmith | 422/82 |

*Primary Examiner*—S. Clement Swisher
*Attorney, Agent, or Firm*—R. J. Steinmeyer; R. R. Meads; T. R. Schulte

[57] ABSTRACT

A method and apparatus for determining an insufficient liquid volume. The invention includes an electromagnetic sensing device in a conduit into which the sample liquid is mixed. The electromagnetic sensing device detects the presence of air in the conduit which indicates that an insufficient liquid volume has been aspirated.

4 Claims, 2 Drawing Figures

METHOD AND APPARATUS FOR DETECTING INSUFFICIENT LIQUID LEVELS

BACKGROUND OF THE INVENTION

1. Field of the Invention

The invention relates to the field of liquid handling apparatus. More particularly, the invention relates to the field of clinical diagnostic equipment. In still greater particularity, the invention relates to the field of clinical diagnostic equipment employing a sample handling apparatus. By way of further characterization, but not by way of limitation thereto, the invention is a detector for determining when an insufficient volume of a liquid has been delivered to an instrument.

2. Description of the Related Art

In the clinical diagnostics area, where samples of various body fluids are tested in order to diagnose various patient illnesses, accuracy is extremely important. Thus, serious problems can arise for a patient if the instrument analyzes a short sample. That is, if less than the expected volume of a bodily fluid such as serum, urine, sweat, cerebrospinal fluid or other sample fluids are injected into the instrument, inaccurate readings may result. Analysis of a short sample can thus cause improper diagnosis and improper medication to be prescribed.

In clinical diagnostic instruments a sample probe is generally utilized to withdraw a sample of liquid from a sample cup. Because most instruments are automated, there is no operator to determine whether the required volume of sample liquid has been withdrawn from the sample cup. In order to ensure that the desired volume of sample liquid had been withdrawn, prior devices have employed conductivity methods which use two or more probes. This method is expensive and complicated. Other devices attempt to determine sample volume with light sensors mounted on the sample probe. While suited for their intended purposes, these devices are expensive and, in many cases, inaccurate.

SUMMARY OF THE INVENTION

The invention is a method and apparatus for detecting insufficient liquid volumes in a sample handling apparatus. If an insufficient sample has been withdrawn from the sample cup, air will also have been picked up and, when the sample is injected into the conduit along with other liquids, air bubbles are generated. By determining the presence of these air bubbles and by measuring the amount of air in the conduit, it can be determined that an insufficient sample volume had been withdrawn from the sample cup by the probe.

The present invention utilizes an electromagnetic sensor adjacent to the conduit in order to determine the presence of air in the conduit. A means for determining the amount of the detected air is operatively associated with the detecting means so as to provide a measure of the detected air. The method and apparatus provide very linear, very accurate, and inexpensive means to determine that an insufficient sample volume had been aspirated from a sample cup.

DESCRIPTION OF THE PREFERRED EMBODIMENT

Figure 1:
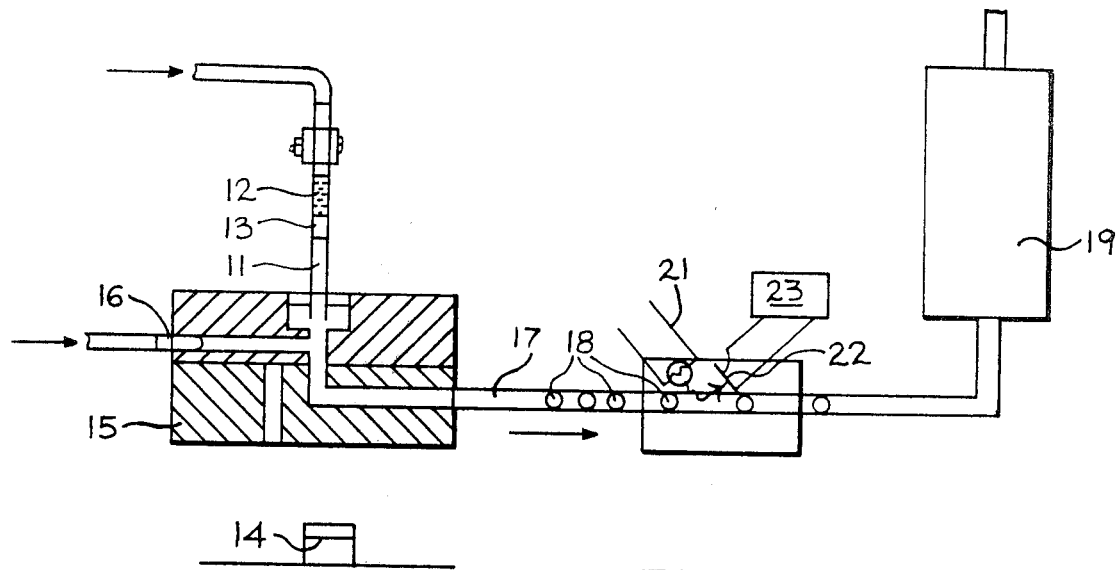
FIG. 1 illustrates the preferred embodiment of the invention for detecting air bubbles in a liquid sampling apparatus.

Referring to FIG. 1, a probe 11 contains a volume of a sample liquid 12 and a volume of air 13. Sample liquid 12 and air volume 13 were withdrawn from a sample cup 14 by a probe 11. That is, probe 11 moves through a sample transfer valve 15 as described in U.S. Pat. No. 4,297,903 issued to E. E. Buzza on Nov. 3, 1981. This patent is specifically incorporated herein by reference and made a part of this specification. Another liquid such as a diluent is injected into sample transfer valve 15 through a port 16. Sample liquid 12, air volume 13 and the diluent are mixed as they are injected into a conduit 17. Upon mixing, air volume 13 is dispersed into a plurality of air bubbles 18. These air bubbles 18 are carried through conduit 17 to a flow cell 19. As air bubbles 18 pass through conduit 17 they are detected by an electromagnetic sensor which may include a light source 21 and a light detector 22 on the same side of conduit 17. Light detector 22 is connected to a determining means such as a microprocessor 23 where the number of air bubbles 18 are counted.

Figure 2:
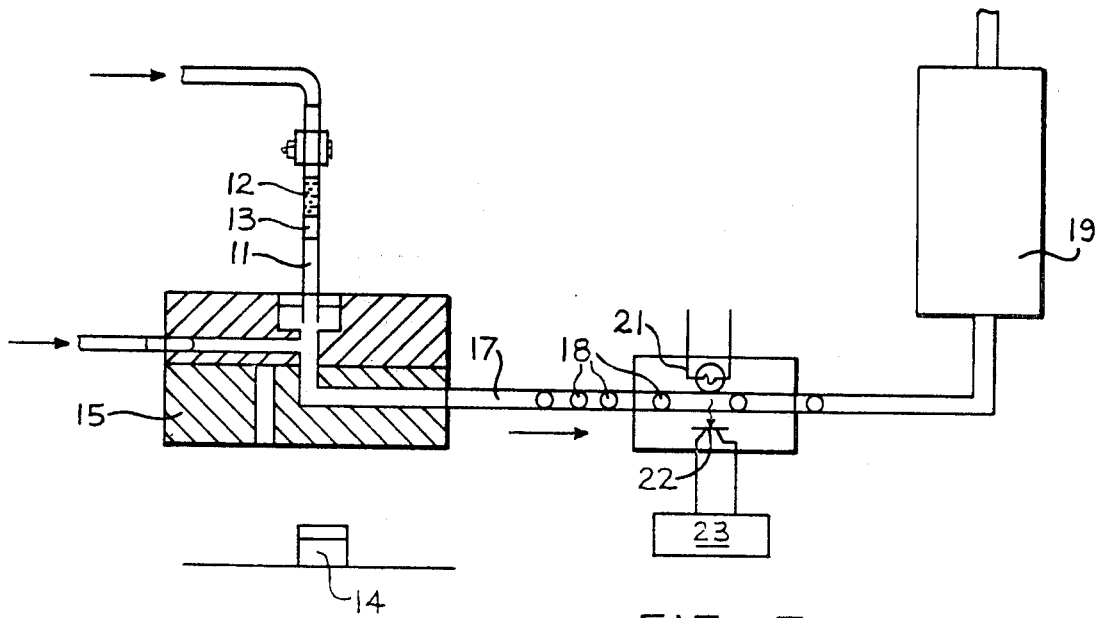
FIG. 2 illustrates an alternate embodiment of the invention for detecting air bubbles in a liquid sampling apparatus.

Referring to FIG. 2, the elements are the same as in FIG. 1 except that the placement of light source 21 and light detector 22 is altered. That is, in the alternate embodiment shown in FIG. 2, light source 21 is placed on one side of conduit 17 while the light detector is placed on the opposite side of conduit 17. Thus, light from light source 21 is directed through conduit 17 and the liquid or air bubbles 18 to light detector 22.

Mode of Operation

Referring to FIG. 1, when the combined liquids and air bubbles 18 pass through conduit 17, light source 21 and light detector 22 detect the presence of air bubbles 18 in the fluid stream in conduit 17. That is, if serum sample 12 is incomplete in that an air volume 13 is included therewith, upon mixing of air volume 13 with the diluent, air bubbles 18 are generated due to the fact that air and liquid cannot mix homogeneously. Air bubbles 18 are passed at intervals through conduit 17. Because of the difference in the indices of refraction of the liquids and air bubbles 18, the amount of light received by light detector 22 varies with the passing of air bubbles 18 as opposed to a liquid stream. In FIG. 1, light source 21 and light detector 22 are placed on the same side of conduit 17 such that light from light source 21 which is reflected and refracted in conduit 17 by the liquid stream and by air bubbles 18 is detected by light detector 22. The output from detector 22 is fed to microprocessor 23 where the number of air bubbles are determined. The lack of sufficient sample is directly proportional to the number of air bubbles.

While particular forms of the invention have been disclosed with respect to a preferred embodiment thereof, it is not to be so limited as changes and modifications may be made which are within the full intended scope of the invention as defined by the appended claims. In particular, the invention can be modified as shown in FIG. 2. That is, the location of the electromagnetic sensing means may be altered such that the light source and detector are on the same side of conduit 17 as in FIG. 1 or on opposite sides of conduit 17 as in FIG. 2. The embodiment disclosed in FIG. 1 is preferred in that greater sensitivity and accuracy are attained when light source 21 and light detector 22 are on the same side of conduit 17. With light source 21 and light detector 22 on the same side of conduit 17, the conduit diameter is not critical. That is, if source 21 and detector 22 are on opposite sides of conduit 17, the conduit diameter must be uniform or false readings may result from air outside the conduit. In addition, with the detector on the same side, light need only pass through one side of the conduit rather than through both walls of conduit 17.

Other alternate embodiments of the invention may include varying the diameter of the probe such that a very accurate microvolume measuring system could be designed allowing the probe volume to be measured and used as a standard. That is, if exact probe volume is known, the number of air bubbles detected would indicate the exact volume withdrawn. The invention allows very linear, accurate, and inexpensive means to detect when an insufficient volume of a sample or other liquid has been aspirated by a probe. The disclosed method and apparatus does not interfere with the liquid or contact it in any way and thus allows for a nonintrusive type of determination. This eliminates the need for conductivity type determinations or other determinations which may affect the efficiency of the instrument or the integrity of the sample liquid.

What is claimed is:

1. In a liquid sampling apparatus including a probe for withdrawing a first liquid volume from a container, a conduit into which said liquid volume may be expelled, and a source of a second liquid volume connected to said conduit, said second liquid volume to be mixed with said first liquid volume thereby generating air bubbles if said liquid volumes are insufficient; a device for detecting said insufficient volumes comprising:
   electromagnetic means, associated with said conduit, for detecting the presence of said air bubbles; and
   means, responsive to said detecting means, for counting said detected air bubbles.

2. Apparatus according to claim 1 wherein said electromagnetic means includes:
   a light source; and
   a light detector located on the same side of said conduit as said light source.

3. Apparatus according to claim 1 wherein said electromagnetic means includes:
   a light source; and
   a light detector located on the opposite side of said conduit from said light source.

4. A method for determining an insufficient liquid volume in a liquid sampling apparatus comprising the steps of:
   aspirating a volume of a first liquid from a container;
   mixing said aspirated volume with a second liquid volume thereby generating air bubbles if said liquid volumes are insufficient;
   conducting said mixed first and second liquids and said air bubbles through a conduit;
   electromagnetically detecting the presence of said air bubbles in said conduit; and
   counting said air bubbles.

* * * * *